US008007542B2

(12) United States Patent
Hiles et al.

(10) Patent No.: US 8,007,542 B2
(45) Date of Patent: Aug. 30, 2011

(54) FREEZE-DRIED COLLAGENOUS BIOMATERIAL MEDICAL SPONGE DEVICE

(75) Inventors: Michael C. Hiles, Lafayette, IN (US); Umesh H. Patel, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 527 days.

(21) Appl. No.: 11/931,556

(22) Filed: Oct. 31, 2007

(65) Prior Publication Data
US 2008/0145395 A1 Jun. 19, 2008

Related U.S. Application Data

(63) Continuation of application No. 10/744,420, filed on Dec. 23, 2003, now Pat. No. 7,699,895, which is a continuation of application No. 09/320,933, filed on May 27, 1999, now Pat. No. 6,666,892, which is a continuation-in-part of application No. 08/916,490, filed on Aug. 22, 1997, now Pat. No. 6,206,931.

(60) Provisional application No. 60/110,407, filed on Dec. 1, 1998, provisional application No. 60/024,693, filed on Sep. 6, 1996, provisional application No. 60/024,542, filed on Aug. 23, 1996.

(51) Int. Cl.
*A61F 2/02* (2006.01)
(52) U.S. Cl. .............. 623/23.72; 623/23.75; 623/901; 623/11.11; 424/426
(58) Field of Classification Search ............... None
See application file for complete search history.

(56) References Cited

U.S. PATENT DOCUMENTS

| | | | |
|---|---|---|---|
| 2,172,903 A | 9/1939 | Charping | |
| 3,346,401 A | 10/1967 | Barat et al. | |
| 3,562,820 A | 2/1971 | Bernhard | |
| 3,632,361 A | 1/1972 | Battista | |
| 3,649,163 A | 3/1972 | McCusker | |
| 3,810,473 A | 5/1974 | Cruz et al. | |
| 4,193,813 A | 3/1980 | Chvapil | |
| 4,292,972 A | 10/1981 | Pawelchak et al. | |
| 4,320,201 A | 3/1982 | Berg et al. | |
| 4,347,234 A | 8/1982 | Wahlig et al. | |
| 4,394,370 A | 7/1983 | Jeffries | |
| 4,404,970 A | 9/1983 | Sawyer | |
| 4,409,332 A | 10/1983 | Jeffries et al. | |
| 4,412,947 A | 11/1983 | Cioca | |
| 4,472,840 A | 9/1984 | Jeffries | |
| 4,578,067 A | 3/1986 | Cruz | |
| 4,606,337 A | 8/1986 | Zimmerman et al. | |
| 4,681,588 A | 7/1987 | Ketharanathan | |
| 4,755,593 A | 7/1988 | Lauren | |
| 4,798,611 A | 1/1989 | Freeman | |
| 4,801,299 A | 1/1989 | Brendel et al. | |
| 4,813,958 A | 3/1989 | Dixon | |
| 4,837,379 A | 6/1989 | Weinberg | |
| 4,838,888 A | 6/1989 | Nashef | |
| 4,885,005 A | 12/1989 | Nashef et al. | |
| 4,891,359 A | 1/1990 | Saferstein et al. | |
| 4,902,508 A | 2/1990 | Badylak et al. | |
| 4,925,924 A | 5/1990 | Silver et al. | |
| 4,948,540 A | 8/1990 | Nigam | |
| 4,950,483 A | 8/1990 | Ksander et al. | |
| 4,956,178 A | 9/1990 | Badylak et al. | |
| 4,969,912 A | 11/1990 | Kelman et al. | |
| 4,970,298 A | 11/1990 | Silver et al. | |
| 4,976,733 A | 12/1990 | Girardot | |
| 4,994,084 A | 2/1991 | Brennan | |
| 5,024,841 A | 6/1991 | Chu et al. | |
| 5,028,695 A | 7/1991 | Eckmayer et al. | |
| 5,071,436 A | 12/1991 | Huc et al. | |
| 5,094,661 A | 3/1992 | Levy et al. | |
| 5,106,949 A | 4/1992 | Kemp et al. | |
| 5,141,747 A | 8/1992 | Scholz | |
| 5,171,574 A | 12/1992 | Kuberasampath et al. | |
| 5,206,023 A | 4/1993 | Hunziker | |
| 5,206,028 A | 4/1993 | Li | |
| 5,215,541 A | 6/1993 | Nashef et al. | |
| 5,219,576 A | 6/1993 | Chu et al. | |
| 5,256,418 A | 10/1993 | Kemp | |
| 5,275,826 A | 1/1994 | Badylak et al. | |
| 5,279,612 A | 1/1994 | Eberhardt | |
| 5,281,422 A | 1/1994 | Badylak et al. | |

(Continued)

FOREIGN PATENT DOCUMENTS

GB 2266239 10/1993

(Continued)

OTHER PUBLICATIONS

"Guideline on Validation of the Limulus Amebocyte Lysate Test as an End-Product Endotoxin Test for Human and Animal Parenteral Drugs, Biological Products, and Medical Devices". Dec. 1997. Ctr for Drug Evaluation & Research, Ctr for Biologic Evaluation & Research, Ctr for Devices & Radiological Health and Ctr for Veterinary Medicine.

American National Standard, ANSI/AAMI 10993-1:1994. "Biological Evaluation of Medical Devices—Part 1: Guidance on Selection of Tests". Association for the Advancement of Medical Instrumentation. pp. 9-17.

Badylak, S.F. et al.: "the Use of Xenogeneic Small Intestinal Submucosa as a Biomaterial for Achille's Tendon Repair in a Dog Model"; Journal of Biomedical Matrials Research, vol. 29, No. 8, 1995, pp. 977-985, XP002071882.

Block, S. "Peroxygen Compounds", Disinfection, Sterilization and Preservation, 5th Edition 2001. pp. 185-204. Lippincott Williams & Wilkins, Philadephia, PA.

Clarke, K.M., et al. "Intestine Submucosa and Polypropylene Mesh for Abdominal Wall Repair in Dogs". The Journal of Surgical Research. Jan. 1996. vol. 60, No. 1. pp. 107-114.

Cobb, M.S. et al.: "Histology After Dural Grafting With Small Inestinal Submucosa", Surgical Neurology, vol. 46, No. 4, 1996, pp. 389-394, XP00201883.

(Continued)

*Primary Examiner* — Allison Ford
(74) *Attorney, Agent, or Firm* — Woodard, Emhardt, Moriarty, McNett & Henry LLP

(57) ABSTRACT

The invention involves a submucosa tissue that has the capability of being shape formed or shape configured. The submucosa involves a purified form of submucosa tissue. Optionally, the submucosa can be packaged in such a manner to permit sterility or maintain sterility of the submucosa.

21 Claims, 1 Drawing Sheet

U.S. PATENT DOCUMENTS

| | | |
|---|---|---|
| 5,298,222 A | 3/1994 | O'Leary |
| 5,336,616 A | 8/1994 | Livesey et al. |
| 5,352,463 A | 10/1994 | Badylak et al. |
| 5,368,608 A | 11/1994 | Levy et al. |
| 5,372,821 A | 12/1994 | Badylak et al. |
| 5,374,515 A | 12/1994 | Parenteau et al. |
| 5,397,352 A | 3/1995 | Burres |
| 5,411,887 A | 5/1995 | Sojander |
| 5,413,791 A | 5/1995 | Rhee et al. |
| 5,437,287 A | 8/1995 | Phillips et al. |
| 5,445,833 A | 8/1995 | Badylak et al. |
| 5,446,462 A | 8/1995 | Cleveland |
| 5,447,536 A | 9/1995 | Girardot et al. |
| 5,451,406 A | 9/1995 | Lawin et al. |
| 5,456,693 A | 10/1995 | Conston et al. |
| 5,457,093 A | 10/1995 | Cini et al. |
| 5,460,962 A | 10/1995 | Kemp |
| 5,466,462 A | 11/1995 | Rosenthal et al. |
| 5,476,516 A | 12/1995 | Seifter et al. |
| 5,480,424 A | 1/1996 | Cox |
| 5,480,427 A | 1/1996 | Kelman et al. |
| 5,489,022 A | 2/1996 | Baker |
| 5,489,261 A | 2/1996 | Franzblau et al. |
| 5,498,420 A | 3/1996 | Mentrup et al. |
| 5,501,706 A | 3/1996 | Arenberg |
| 5,507,810 A | 4/1996 | Prewett et al. |
| 5,510,121 A | 4/1996 | Rhee et al. |
| 5,510,418 A | 4/1996 | Rhee et al. |
| 5,512,291 A | 4/1996 | Li |
| 5,514,181 A | 5/1996 | Light et al. |
| 5,516,395 A | 5/1996 | Anhauser et al. |
| 5,520,925 A | 5/1996 | Maser |
| 5,522,840 A | 6/1996 | Krajicek |
| 5,531,786 A | 7/1996 | Perry et al. |
| 5,531,791 A | 7/1996 | Wolfinbarger |
| 5,554,389 A | 9/1996 | Badylak et al. |
| 5,565,210 A | 10/1996 | Rosenthal et al. |
| 5,567,806 A | 10/1996 | Abdul-Malak et al. |
| 5,571,181 A | 11/1996 | Li |
| 5,607,476 A | 3/1997 | Prewett et al. |
| 5,607,590 A | 3/1997 | Shimizu |
| 5,641,518 A | 6/1997 | Badylak et al. |
| 5,645,860 A | 7/1997 | Knapp et al. |
| 5,693,085 A | 12/1997 | Buirge et al. |
| 5,695,998 A | 12/1997 | Badylak et al. |
| 5,707,962 A | 1/1998 | Chen et al. |
| 5,711,969 A | 1/1998 | Patel et al. |
| 5,733,337 A | 3/1998 | Carr et al. |
| 5,755,791 A | 5/1998 | Whitson et al. |
| 5,762,966 A | 6/1998 | Knapp et al. |
| 5,782,914 A | 7/1998 | Schankereli |
| 5,866,414 A | 2/1999 | Badylak et al. |
| 5,885,619 A | 3/1999 | Patel et al. |
| 5,955,110 A | 9/1999 | Patel et al. |
| 6,099,567 A | 8/2000 | Badylak et al. |
| 6,206,931 B1 | 3/2001 | Cook et al. |
| 6,358,284 B1 | 3/2002 | Fearnot |
| 6,475,232 B1 | 11/2002 | Babbs et al. |
| 6,666,892 B2 | 12/2003 | Hiles et al. |
| 7,029,434 B2 | 4/2006 | Carpentier et al. |
| 2002/0048595 A1 | 4/2002 | Geistlich et al. |

FOREIGN PATENT DOCUMENTS

| | | | |
|---|---|---|---|
| WO | WO 85/04413 | | 10/1985 |
| WO | WO 90/00060 | * | 1/1990 |
| WO | WO 95/22611 | | 8/1995 |
| WO | WO 96/24661 | | 8/1996 |
| WO | WO 96/25179 | | 8/1996 |
| WO | WO 96/31157 | | 10/1996 |
| WO | WO 96/32146 | | 10/1996 |
| WO | WO 98/22158 | | 5/1998 |
| WO | WO 98/25545 | | 6/1998 |
| WO | WO 98/25636 | | 6/1998 |
| WO | WO 98/25637 | | 6/1998 |
| WO | WO 98/26291 | | 6/1998 |
| WO | WO 00/32250 | | 6/2000 |

OTHER PUBLICATIONS

Denton, F.W., "Chlorhexidine", Disinfection, Sterilization and Preservation, S. Block, editor, 5th Edition 2001. pp. 321-336. Lippincott Williams & Wilkins, Philadephia, PA.

Hawley's Condensed Chemical Dictionary, Eleventh Edition, Van Nostrand Reinhold Company, (1987), pp. 886 and 890.

Hodde, J.P. et al., "Gycosaminoglycan Content of Small Intestinal Submucosa: A Bioscaffold for Tissue Replacement" Tissue Engineering, vol. 2, No. 3, 1996, pp. 209-217 XP002063373.

Kropp, B.P., et al. "Regenerative Urinary Bladder Augmentation Using Small Intestinal Submucosa: Urodynamic and Histopathologic Assessment in Long-Term Canine Bladder Augmentations". The Journal of Urology. Jun. 1996. vol. 155, No. 6. pp. 2098-2104.

Kropp, B.P., et al. "Experimental Assessment of Small Intestinal Submucosa as a Bladder Wall Substitute". Urology. Sep. 1995. vol. 46, No. 3. pp. 396-400.

Prevel, C.D., et al. "Small Intestinal Submucosa: Utilization as a Wound Dressing in Full-Thickness Rodent Wounds". Annals of Plastic. Surgery. Oct. 1995. vol. 35, No. 4. pp. 381-388.

Prevel, C.D., et al. "Small Intestinal Submucosa: Utilization for Repair of Rodent Abdominal Wall Defects". Annals of Plastic. Surgery. Oct. 1995. vol. 35, No. 4. pp. 374-380.

Vaught, J.D. et al.; "Detrusor Regeneration in the Rat Using Porcine Small Intestinal Submucosal Grafts: Functional Innervation and Receptor Expression", The Journal of Urology, vol. 155, No. 1, 1996, pp. 374-378, XP002071884.

Wikipedia online definition for "collagen".

European Search Report EP 08008810 dated Jun. 27, 2008.

D Horak et al: Hydrogels in endovascular embolization. III. Radiopaque spherical particles, their preparation and properties: Biomaterials, GB, Elsevier Sciences Publishers BV., Barking, vol. 2, No. 8 Mar. 1, 1987, pp. 142-145.

European Search Report, Patent Application No. 08012454.8, dated Jun. 17, 2008.

* cited by examiner

FREEZE-DRIED COLLAGENOUS BIOMATERIAL MEDICAL SPONGE DEVICE

REFERENCE TO RELATED APPLICATION

The present application is a continuation patent application of U.S. patent application Ser. No. 10/744,420 filed Dec. 23, 2003, which claims priority to U.S. patent application Ser. No. 09/320,993 filed May 27, 1999, now U.S. Pat. No. 6,666,892, both entitled A MULTI-FORMED COLLAGENOUS BIOMATERIAL MEDICAL DEVICE, which claims the benefit of U.S. Provisional Patent Application Ser. No. 60/110,407 filed Dec. 1, 1998, entitled RADIOPAQUE IMPLANTABLE COLLAGENOUS BIOMATERIAL DEVICE and which is a continuation-in-part of U.S. patent application Ser. No. 08/916,490 filed Aug. 22, 1997, now U.S. Pat. No. 6,206,931, entitled GRAFT PROSTHESIS, MATERIALS AND METHODS, which claims the benefit of U.S. Provisional Patent Application Ser. No. 60/024,542 filed Aug. 23, 1996 entitled SUBSTANTIALLY PURIFIED TELA SUBMUCOSA IMPLANTABLE TISSUE and U.S. Provisional Patent Application Ser. No. 60/024,693 filed Sep. 6, 1996 entitled GRAFT PROSTHESIS, MATERIALS AND METHODS.

TECHNICAL FIELD

The invention generally relates to a medical device and in particular, to a medical device comprising a collagenous biomaterial.

BACKGROUND OF THE INVENTION

A naturally occurring biomaterial for medical implantation is more desirable that a synthetic implant. Synthetic implants tend to cause adverse reactions in a patient, including thrombosis, immune responses, and potentially restenosis in vascular applications. Therefore, a medical implant that reduces or eliminates these problems is a technical advance.

Collagenous biomaterials are known to be used in medical applications as medical devices. As a naturally occurring biomaterial, the implant produces less complications than a synthetic implant. Collagen is used as an abundant source of protein, and is most notably derived from bovine skin. Collagen forms a matrix that is useable as an implant. However, as a biomaterial, it does not have good manipulation properties, unless treated in other ways. In addition, one problem with these material is that collagen biomaterials also carry with them antigens which cause an immune response in the patient. Therefore, a product that behaves like collagen in vivo yet is highly manipulative and elicits less to no negative immune response is a technical achievement.

SUMMARY OF THE INVENTION

The foregoing problems are solved and a technical advance is achieved with the present invention. A new biomaterial comprising the submucosa of a tissue was discovered to have greater benefit than using collagen. For example, the submucosa is shown to exhibit more remodeling, regrowth, and regeneration of tissue upon implant. It has been shown that submucosal tissue is absorbed by the patient and thus the patient does not require post-implantation procedures to remove the implant. The submucosal tissue has been shown to elicit favorable immune response that leads to an accommodation of the submucosal implant versus a rejection based response. Therefore, to further improve the submucosal tissue's industrial utility, the applicants have discovered that this utility can be achieved by improving the submucosa's purity and forming the submucosal tissue into various forms. Such forms, include, but are not limited to sheets, sponges, fluidized, etc. The present invention relates to a purified form of submucosal tissue that is treated in such a manner as to confer some shape memory and shape configuration to the implant. However, the submucosal tissues are not limited to implants and can be formed to be used in topical applications as well, such as wound dressings or wound plugs.

In addition, the problem of maintaining the sterility of the medical device is solved by including the medical device in a pouch or plurality of pouches. The pouches can be at least one of a gas permeable, sealed, hermetically sealed, sterile, UV protected, and multiple pouched. In addition, the foregoing problems are solved by including processes of making the medical device.

DETAILED DESCRIPTION

Figure 1:
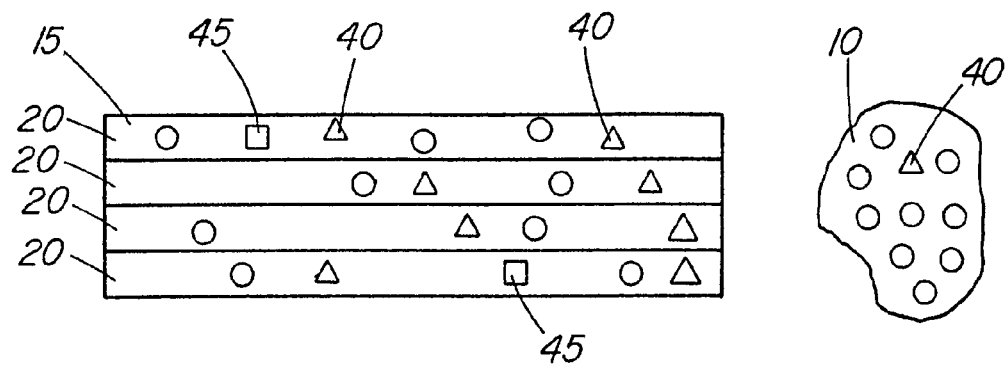
FIG. 1 shows two aspects of the invention as the biomaterial multilaminate sheet or in sponge forms.

In the discussions herein, a number of terms are used. In order to provide a clear and consistent understanding of the specification and claims, the following definitions are provided.

Bioburden—refers to the number of living microorganisms, reported in colony-forming units (CFU), found on and/or in a given amount of material. Illustrative microorganisms include bacteria, fungi, and their spores.

Disinfection—refers to a reduction in the bioburden of a material.

Sterile—refers to a condition wherein a material has a bioburden such that the probability of having one living microorganism (CFU) on and/or in a given section of the material is one in one-million or less.

Pyrogen—refers to a substance which produces febrile response after introduction into a host.

Endotoxin—refers to a particular pyrogen which is part of the cell wall of gram-negative bacteria. Endotoxins are continually shed from the bacteria and contaminate materials.

Purification—refers to the treatment of a material to remove one or more contaminants which occur with the material, for instance contaminants with which the material occurs in nature, and/or microorganisms or components thereof occurring on the material. Illustratively, the contaminants may be those known to cause toxicity, infectivity, pyrogenicity, irritation potential, reactivity, hemolytic activity, carcinogenicity and/or immunogenicity.

Biocompatibility—refers to the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests assay as to a material's toxicity, infectivity, pyrogenicity, irritation potential, reactivity, hemolytic activity, carcinogenicity, and/or immunogenicity. A biocompatible structure or material when introduced into a majority of patients will not cause an adverse reaction or response. In addition, it is contemplated that biocompatibility can be effected by other contaminants such as prions, surfactants, oligonucleotides, and other biocompatibility effecting agents or contaminants.

Contaminant—refers to an unwanted substance on, attached to, or within a material. This includes, but is not limited to: bioburden, endotoxins, processing agents such as antimicrobial agents, blood, blood components, viruses, DNA, RNA, spores, fragments of unwanted tissue layers, cellular debris, and mucosa.

Tela submucosa—refers to a layer of collagen-containing connective tissue occurring under the mucosa in most parts of the alimentary, respiratory, urinary, integumentary, and genital tracts of animals.

The invention is generally directed to a medical device, comprising a collagenous biomaterial (also referred to as collagen-based matrices, tissue mucosa, tissue submucosa, intestines, biomaterial) and is further described in the non-limiting disclosure set forth below.

One such collagenous biomaterial includes tissue mucosa, which also further includes a tissue submucosa, which further includes a small intestine submucosa (SIS), also described herein as tela submucosa. Tela submucosa is a multi-laminate structure, comprising the tunica submucosa, lamina muscularis mucosa, and the stratum compactum. Collagenous materials can also have biotropic agents comprising at least one of a proteoglycan, glycosaminoglycan, and growth factor. The SIS can be made using the techniques described in Cook et al., WIPO Publication WO 98/22158, dated 28 May 1998, which is the published application of PCT/US97/14855, the disclosure of which is set forth below.

One type of collagenous mucosa is tela submucosa, and as with many animal tissues, is generally aseptic in its natural state, provided the human or animal does not have an infection or disease. This is particularly the case since the tela submucosa is an internal layer within the alimentary, integumentary, respiratory, urinary, and genital tracts of animals. Accordingly, it is generally not exposed to bacteria and other cellular debris such as the epithelium of the intestinal tract. One feature of the present invention is the discovery that by disinfecting the source tissue for the tela submucosa prior to delamination, the aseptic state of the tela submucosa layer can be preserved or substantially preserved, particularly if the delamination process occurs under sterile conditions.

Other sources of mucosa exist. For example, the mucosa can also be derived from vertebrate liver tissue as described in WIPO Publication, WO 98/25637, based on PCT application PCT/US97/22727; from gastric mucosa as described in WIPO Publication, WO 98/26291, based on PCT application PCT/US97/22729; from stomach mucosa as described in WIPO Publication, WO 98/25636, based on PCT application PCT/US97/23010; or from urinary bladder mucosa as described in U.S. Pat. No. 5,554,389; the disclosures of all are expressly incorporated herein.

In particular, it has been discovered that disinfecting the tela submucosa source, followed by removal of a purified biomaterial including the tela submucosa, e.g. by delaminating the tela submucosa from the tunica muscularis and the tunica mucosa, minimizes the exposure of the tela submucosa to bacteria and other contaminants. In turn, this enables minimizing exposure of the isolated tela submucosa biomaterial to disinfectants or sterilants if desired, thus substantially preserving the inherent biochemistry of the tela submucosa and many of the tela submucosa's beneficial effects.

A tela submucosa implantable collagen biomaterial according to the present invention can, as indicated above, be obtained from the alimentary, respiratory, urinary, integumentary, or genital tracts of animals. Preferably, the tela submucosa tissues, which are collagen-based and thus predominantly collagen, are derived from the alimentary tract of mammals, such as cows, sheep, dogs, and most preferably from the intestinal tract of pigs. A most preferred source of whole small intestine is harvested from mature adult pigs weighing greater than about 450 pounds. Intestines harvested from healthy, non-diseased animals will contain blood vessels and blood supply within the intestinal tract, as well as various microbes such as *E. coli* contained within the lumen of the intestines. Therefore, disinfecting the whole intestine prior to delamination of the tela submucosa substantially removes these contaminants and provides a preferred implantable tela submucosa tissue which is substantially free of blood and blood components as well as any other microbial organisms, pyrogens or other pathogens that may be present. In effect, this procedure is believed to substantially preserve the inherent aseptic state of the tela submucosa, although it should be understood that it is not intended that the present invention be limited by any theory. All that is required or be met is that the biomaterial satisfies the above-mentioned criteria.

It is also desirable that the collagenous biomaterial according to the present invention be substantially free of any antiviral agents or any antimicrobial type agents which can affect the biochemistry of the biomaterial and its efficacy upon implantation. In the past, one method of treating such tissue material is to rinse the delaminated tissue in saline and soak it in an antimicrobial agent, for example, as disclosed in U.S. Pat. No. 4,956,178. While such techniques can optionally be practiced with isolated collagenous mucosa or submucosa of the present invention, preferred processes according to the present invention avoid the use of antimicrobial agents and the like which can not only affect the biochemistry of the collagenous biomaterial but also can be unnecessarily introduced into the tissues of the patient.

As discussed above, it has been discovered that a highly pure form of an implantable tela submucosa collagen biomaterial can be obtained by first disinfecting a tela submucosa source prior to removing a purified collagen biomaterial including the tela submucosa layer, e.g. by delaminating the tela submucosa source. It has also been discovered that certain processing advantages as well as improved properties of the resultant tela submucosa layer are obtained by this process, including greater ease in removing attached tissues from the submucosa layer, and a characteristic, low contaminant profile.

Processes of the invention desirably involve first rinsing the tela submucosa source one or more times with a solvent, suitably water. The rinsing step is followed by treatment with a disinfecting agent. The disinfecting agent is desirably an oxidizing agent. Preferred disinfecting agents are peroxy compounds, preferably organic peroxy compounds, and more preferably peracids. Such disinfecting agents are desirably used in a liquid medium, preferably a solution, having a pH of about 1.5 to about 10, more preferably a pH of about 2 to about 6, and most preferably a pH of about 2 to about 4. In methods of the present invention, the disinfecting agent will generally be used under conditions and for a period of time which provide the recovery of characteristic, purified submucosa matrices as described herein, preferably exhibiting a bioburden of essentially zero and/or essential freedom from pyrogens. In this regard, desirable processes of the invention involve immersing the tissue source (e.g. by submersing or showering) in a liquid medium containing the disinfecting agent for a period of at least about 5 minutes, typically in the range of about 5 minutes to about 40 hours, and more typically in the range of about 0.5 hours to about 5 hours.

A preferred peroxy disinfecting agent is hydrogen peroxide. The concentration of hydrogen peroxide can range from about 0.05% to 30% by volume. More preferably the hydrogen peroxide concentration is from about 1% to 10% by volume and most preferably from about 2% to 5% by volume. The solution can or can not be buffered to a pH from about 5 to 9. More preferably the pH is from about 6 to 7.5. These concentrations can be diluted in water or in an aqueous solution of about 2% to about 30% by volume alcohol. Most preferably the alcohol is ethanol. The solution temperature can range from about 15 to 50° C. More preferably the solution temperature is from about 20 to 40° C. Most preferably, the solution temperature is from about 32 to 37° C. The exposure time can range from about 10 to 400 minutes. Preferably, the exposure time is from about 120 to 240 minutes. More preferably, the exposure time is from 180 to 210 minutes.

A preferred organic peroxide disinfecting agent is perpropionic acid. The concentration of perpropionic acid can range from about 0.1% to 10% by volume. More preferably the perpropionic acid concentration is from about 0.1% to 1.0% by volume and most preferably from about 0.2% to 0.5% by volume. These concentrations of perpropionic acid can be diluted in water or in an aqueous solution of about 2% to about 30% by volume alcohol. Most preferably the alcohol is ethanol. The tela submucosa tissue source can be exposed to the organic peroxide solution for periods from about 15 minutes to about 40 hours, and more typically in the range of about 0.5 hours to about 8 hours. Other peroxy disinfecting agents are suitable for use as described in "Peroxygen Compounds"., S. Block, in *Disinfection, Sterilization and Preservation*, S. Block, Editor, 4th Edition, Philadelphia, Lea & Febiger, pp. 167-181, 1991; and "Disinfection with peroxygens", M. G. C. Baldry and J. A. L. Fraser, in *Industrial Biocides*, K. Payne, Editor, New York, John Wiley and Sons, pp. 91-116, 1988.

Another oxidizing disinfecting agent is chlorhexidine (1,6-di(4-chlorophenyidiguanido)hexane) in its digluconate form. The concentration of chlorhexidine digluconate can range from about 0.1% to 15% by weight. More preferably, the chlorhexidine digluconate concentration is from about 0.1% to 2% by weight and most preferably from about 0.2% to 5% by weight. The solution can or can not be buffered to a pH from about 5 to 8. More preferably the pH is from about 5.5 to 7. These concentrations can be diluted in water or in an aqueous solution of about 2% to about 20% by volume alcohol. Most preferably the alcohol is ethanol at a concentration of about 5% to 10%. The solution temperature can range from about 15 to 30° C. The exposure time can range from about 10 to 400 minutes. More preferably the exposure time is from about 30 to 60 minutes. Other chlorine agents are described in "Chlorhexidine", G. W. Denton, in *Disinfection, Sterilization and Preservation*, S. Block, Editor, 4th Edition, Philadelphia, Lea & Febiger, pp. 274-289, 1991.

In preferred preparative processes, a peracid or other disinfecting agent can be dissolved in a dilute aqueous alcohol solution, preferably wherein the alcohol has from 1 to about 6 carbon atoms, and wherein the alcohol can generally comprise from about 1% to about 30% by volume of the solution. More preferred alcohols for use in the invention are selected from the group consisting of ethanol, propanols and butanols. Ethanol is a preferred alcohol for these purposes.

When a peracid is used in the disinfection, it is preferably selected from the group consisting of peracetic acid, perpropionic acid or perbenzoic acid. Peracetic acid is the most preferred disinfecting agent. The peracetic acid is preferably diluted into about a 2% to about 10% by volume alcohol solution. The concentration of the peracetic acid can range, for example, from about 0.05% by volume to about 1.0% by volume. Most preferably the concentration of the peracetic acid is from about 0.1% to about 0.3% by volume. Hydrogen peroxide can also be used as a disinfecting agent. Alternatively, or in addition, the tela submucosa tissue source, e.g. from small intestine, can be disinfected utilizing disinfecting agents such as glutaraldehyde, formalin and the like, which are also known for their ability to introduce substantial crosslinking into collagen matrices, in contrast to the action of other disinfecting agents such as peracids which can be used to disinfect without introducing such crosslinking. Additionally, the tela submucosa source can be treated with radiation, e.g., gamma radiation, for purposes of disinfection.

Variations on the disinfection process can also include the following:

1. Intestine is treated with 0.2% peracetic acid, 5% ethanol solution at a ratio of 10:1 solution to intestine ratio by weight. Solution has a pH of 2.6. Solution and intestine are vigorously mixed for two hours.
2. Intestine is treated with 1% peracetic acid, 25% ethanol solution at a ration of 5:1 solution to intestine ratio by weight. Solution has a pH of 2. Solution and intestine are vigorously mixed for one hour.
3. Intestine is treated with 1% peracetic acid, 15% ethanol, and 10% hydrogen peroxide solution at a ratio of 5:1 solution to intestine ratio by weight. Solution and intestine are vigorously mixed for one hour.
4. Whole small intestine is rinsed four times with high purity water for 15 minutes. The intestine is then subjected to 1.5 MRAD Electron Beam radiation.
5. Whole small intestine is rinsed four times with high purity water for 15 minutes. Lengthwise along a conveyor belt, the intestine is subjected to high-intensity pulsed light which disinfects the intestine.

Following the treatment as described above, the tela submucosa layer is delaminated from its source, e.g., whole intestine, cow uterus and the like. It has been found that by following this post-disinfection-stripping procedure, it is easier to separate the tela submucosa layer from the attached tissues, e.g. at least from attached tunica muscularis tissue, as compared to stripping the tela submucosa layer prior to disinfection. Moreover it has been discovered that the resultant tela submucosa layer in its most preferred form exhibits superior histology, in that there is less attached tissue and debris on the surface compared to a tela submucosa layer obtained by first delaminating the tela submucosa layer from its source and then disinfecting the layer. Moreover, a more uniform tela submucosa tissue can be obtained from this process, and a tela submucosa having the same or similar physical and biochemical properties can be obtained more consistently from each separate processing run. Importantly, a highly purified, substantially sterile tela submucosa is obtained by this process. The stripping of the tela submucosa source is preferably carried out by utilizing a disinfected or sterile casing machine, to produce a tela submucosa which is substantially sterile and which has been minimally processed. A suitable casing machine is the Model 3-U-400 Stridhs Universal Machine for Hog Casing, commercially available from the AB Stridhs Maskiner, Götoborg, Sweden. Therefore, the measured bioburden levels are minimal or substantially zero. Of course, other means for delaminating the tela submucosa source can be employed without departing from the present invention, including for example those means well known in the art, including delaminating by hand.

It has also been discovered that more preferred processes according to the present invention, not only will eliminate or significantly reduce contaminants contained in the tela submucosa collagen biomaterial, but also will produce a tissue which exhibits no substantial degradation of physical and mechanical properties, e.g., differential porosity (i.e. wherein one side of the submucosa layer has greater porosity than the other side), and good strength, for example burst strength. Also, it has been discovered that more preferred processes do not affect the differential porosity of the tela submucosa collagen biomaterial, which ultimately affects the level of efficacy of this tissue implant. For example, the tissue is not necessarily treated with a crosslinking agent or a material that disrupts the porosity or inherent, native structure of the collagen biomaterial. Moreover, when hydrogen peroxide is employed, the biomaterial as a whole has greater porosity as well as a higher oxygen content. This helps to ensure the absence of contaminants e.g., endotoxins, pyrogens, and the like.

Preferred collagen-based matrices of the invention, preferably submucosa-containing matrices, are also characterized by the low contaminant levels set forth in Table 1 below, each contaminant level taken individually or in any combination with some or all of the other disclosed contaminant levels. The abbreviations in Table 1 are as follows: CFU/g=colony forming units per gram; PFU/g=plaque forming units per gram; μg/mg=micrograms per milligram; ppm/kg=parts per million per kilogram; and EU/g=endotoxin units per gram.

TABLE 1

| FEATURE | FIRST PREFERRED LEVEL | SECOND PREFERRED LEVEL | THIRD PREFERRED LEVEL |
|---|---|---|---|
| ENDOTOXIN | <12 EU/g | <10 EU/g | <5 EU/g |
| BIOBURDEN | <2 CFU/g | <1 CFU/g | <0.5 CFU/g |
| FUNGUS | <2 CFU/g | <1 CFU/g | <0.5 CFU/g |
| NUCLEIC ACID | <10 μg/mg | <5 μg/mg | <2 μg/mg |
| VIRUS | <500 PFU/g | <50 PFU/g | <5 PFU/g |
| PROCESSING AGENT | <100,000 ppm/kg | <1,000 ppm/kg | <100 ppm/kg |

Even more preferred collagen-based matrices of the invention contain an endotoxin level of less than 1 EU/g, and most preferably less than 0.5 EU/g.

Purified collagen-based matrices according to the present invention can be processed in a number of ways, to provide collagenous matrices useful both in vitro and in vivo. For example, the submucosa can be configured to provide tissue grafts useful in vascular applications, e.g., as generally described in U.S. Pat. Nos. 2,127,903 and 4,902,508.

The tela submucosa of the invention possesses mechanical properties highly desirable for tissue graft materials in vascular applications, including low porosity index, high compliance, and a high burst strength. One skilled in the art will appreciate that the preferred tissue graft material will be of low enough porosity to prevent intraoperative hemorrhage and yet of high enough porosity to allow extension of a newly-developed vasa vasorum through the graft material to nourish the neointimal and luminal surface.

Tela submucosa tissue of the present invention can also be processed to provide fluidized compositions, for instance using techniques as described in U.S. Pat. No. 5,275,826. In this regard, solutions or suspensions of the tela submucosa can be prepared by comminuting and/or digesting the tela submucosa with a protease (e.g. trypsin or pepsin), for a period of time sufficient to solubilize the tissue and form substantially homogeneous solution. The submucosa starting material is desirably comminuted by tearing, cutting, grinding, shearing or the like. Grinding the submucosa in a frozen or freeze-dried state is advantageous, although good results can be obtained as well by subjecting a suspension of pieces of the submucosa to treatment in a high speed blender and dewatering, if necessary, by centrifuging and decanting excess waste. The comminuted tela submucosa can be dried, for example freeze dried, to form a powder. Thereafter, if desired, the powder can be hydrated, that is, combined with water or buffered saline and optionally other pharmaceutically acceptable excipients, to form a fluid tissue graft composition, e.g. having a viscosity of about 2 to about 300,000 cps at 25EC. The higher viscosity graft compositions can have a gel or paste consistency.

Fluidized tela submucosa of this invention finds use as an injectable heterograft for tissues, for example, bone or soft tissues, in need of repair or augmentation most typically to correct trauma or disease-induced tissue defects. The present fluidized submucosa compositions are also used advantageously as a filler for implant constructs comprising, for example, one or more sheets of tela submucosa formed into sealed (sutured) pouches for use in cosmetic or trauma-treating surgical procedures.

In one illustrative preparation, tela submucosa prepared as described herein is reduced to small pieces (e.g. by cutting) which are charged to a flat bottom stainless steel container. Liquid nitrogen is introduced into the container to freeze the specimens, which are then comminuted while in the frozen state to form a coarse tela submucosa powder. Such processing can be carried out, for example, with a manual arbor press with a cylindrical brass ingot placed on top of the frozen specimens. The ingot serves as an interface between the specimens and the arbor of the press. Liquid nitrogen can be added periodically to the tela submucosa specimens to keep them frozen.

Other methods for comminuting tela submucosa specimens can be utilized to produce a tela submucosa powder usable in accordance with the present invention. For example, tela submucosa specimens can be freeze-dried and then ground using a manual arbor press or other grinding means. Alternatively, tela submucosa can be processed in a high shear blender to produce, upon dewatering and drying, a tela submucosa powder.

Further grinding of the tela submucosa powder using a prechilled mortar and pestle can be used to produce a consistent, more finely divided product. Again, liquid nitrogen is used as needed to maintain solid frozen particles during final grinding. The powder can be easily hydrated using, for example, buffered saline to produce a fluidized tissue graft material of this invention at the desired viscosity.

To prepare another preferred fluidized material, a tela submucosa powder can be sifted through a wire mesh, collected, and subjected to proteolytic digestion to form a substantially homogeneous solution. For example, the powder can be digested with 1 mg/ml of pepsin (Sigma Chemical Co., St. Louis, Mo.) and 0.1 M acetic acid, adjusted to pH 2.5 with HCl, over a 48 hour period at room temperature. After this treatment, the reaction medium can be neutralized with sodium hydroxide to inactivate the peptic activity. The solubilized submucosa can then be concentrated by salt precipitation of the solution and separated for further purification and/or freeze drying to form a protease-solubilized intestinal submucosa in powder shape.

Fluidized tela submucosa compositions of this invention find wide application in tissue replacement, augmentation, and/or repair. The fluidized submucosal compositions can be used to induce regrowth of natural connective tissue or bone in an area of an existent defect. By injecting an effective amount of a fluidized submucosa composition into the locale of a tissue defect or a wound in need of healing, one can readily take advantage of the biotropic properties of the tela submucosa. Interestingly, fluidizing SIS by comminution or enzymatic degradation does not result in any appreciable loss of biotropic activities, as shown in U.S. Pat. No. 5,275,826.

It is also possible to shape large surface area constructs by combining two or more tela submucosa segments of the invention, for instance using techniques as described in U.S. Pat. No. 2,127,903 and/or International Publication No. WO 96/32146, dated 17 Oct. 1996, publishing International Application No. PCT/US96/04271, filed 5 Apr. 1996. Thus, a plurality of tela submucosa strips can be fused to one another, for example by compressing overlapping areas of the strips under dehydrating conditions, to form an overall planar construct having a surface area greater than that of any one planar surface of the individual strips used to shape the construct. Shapes can be made by using sutures, staples, biocompatible adhesives such as collagen binding pastes, or dehydrating overlapping structures then heating the structure as described in U.S. Pat. No. 3,562,820.

As described herein, the invention can take many shapes, such as coiled, helical, spring-like, randomized, branched, sheet-like, tubular, spherical, fragmented, fluidized, comminuted, liquefied, suspended, gel-like, injectable, powdered, ground, sheared, and solid material shape.

The tela submucosa powder can be used alone, or in combination with one or more additional bioactive agents such as physiologically compatible minerals, growth factors, antibiotics, chemotherapeutic agents, antigen, antibodies, enzymes, and hormones. Preferably, the powder-form implant will be compressed into a predetermined, three-dimensional shape, which will be implanted into the bone region and will substantially retain its shape during replacement of the graft with endogenous tissues.

Tela submucosa of the invention can also be used as a cell growth substrate, illustratively in sheet, paste or gel shape in combination with nutrients which support the growth of the subject cells, e.g. eukaryotic cells such as endothelial, fibroblastic, fetal skin, osteosarcoma, and adenocarcinoma cells (see, e.g. International Publication No. WO 96/24661 dated 15 Aug. 1996, publishing International Application No. PCT/US96/01842 filed 9 Feb. 1996). In certain forms, the tela submucosa substrate composition will support the proliferation and/or differentiation of mammalian cells, including human cells.

The inventive tela submucosa can also serve as a collagenous biomaterial in compositions for producing transformed cells, (see, e.g., International Publication No. WO 96/25179, dated 22 Aug. 1996, publishing International Application No. PCT/US96/02136 filed 16 Feb. 1996; and International Publication No. WO 95/22611 dated 24 Aug. 1995, publishing International Application No. PCT/US95/02251 filed 21 Feb. 1995). Such compositions for cell transformation will generally include purified tela submucosa of the present invention, for example in fluidized or paste shape as described in U.S. Pat. No. 5,275,826, in combination with a recombinant vector (e.g. a plasmid) containing a nucleic acid sequence with which in vitro or in vivo target cells are to be genetically transformed. The cells targeted for transformation can include, for example, bone progenitor cells.

In order to promote a further understanding of the present invention and its features and advantages, the following specific Examples are provided. It will be understood that these specific Examples are illustrative, and not limiting, of the present invention.

EXAMPLE 1

Thirty feet of whole intestine from a mature adult hog is rinsed with water. This material is then treated in a 0.2% by volume peracetic acid in a 5% by volume aqueous ethanol solution for a period of two hours with agitation. The tela submucosa layer is then delaminated in a disinfected casing machine from the whole intestine. The delaminated tela submucosa is rinsed four (4) times with sterile water and tested for impurities or contaminants such as endotoxins, microbial organisms, and pyrogens. The resultant tissue was found to have essentially zero bioburden level. The tela submucosa layer separated easily and consistently from the whole intestine and was found to have minimal tissue debris on its surface.

EXAMPLE 2

A ten foot section of porcine whole intestine is washed with water. After rinsing, this section of tela submucosa intestinal collagen source material is treated for about two and a half hours in 0.2% peracetic acid by volume in a 5% by volume aqueous ethanol solution with agitation. Following the treatment with peracetic acid, the tela submucosa layer is delaminated from the whole intestine. The resultant tela submucosa is then rinsed four (4) times with sterile water. The bioburden was found to be essentially zero.

EXAMPLE 3

A small section of the tela submucosa intestinal collagen material was subcutaneously implanted in a rat. Within 72 hours, significant angiogenesis was observed.

EXAMPLE 4

Two sections of small intestine are processed by differing methods. The first section is rinsed in tap water, disinfected for 2 hours in a 5% by volume aqueous ethanol solution comprising 0.2% by volume peracetic acid, pH approximately 2.6, delaminated to the tela submucosa, rinsed in purified water, divided into two samples and rapidly frozen. The second section is rinsed in tap water, delaminated to the tela submucosa, rinsed in purified water, placed in a 10% neomycin sulfate solution for 20 minutes (as described in U.S. Pat. No. 4,902,508), rinsed in purified water, divided into two samples and rapidly frozen. The four above-prepared samples are tested for bioburden and endotoxin levels. The first two samples each have bioburdens of less than 0.1 CFU/g and endotoxin levels of less than 0.1 EU/g. The second two samples have respective bioburdens of 1.7 CFU/g and 2.7 CFU/g and respective endotoxin levels of 23.9 EU/g and 15.7 EU/g.

EXAMPLE 5

Three sections of small intestine are processed by differing methods. The first is rinsed in tap water, disinfected for 2 hours in a 5% by volume aqueous ethanol solution comprising 0.2% by volume peracetic acid, pH about 2.6, delaminated to the tela submucosa, rinsed in purified water, and rapidly frozen. The second is rinsed in tap water, delaminated to the tela submucosa, rinsed in purified water, disinfected according to the methods of Example 1 in U.S. Pat. No. 5,460,962 (treatment for 40 hours in a 0.1% by volume aqueous solution of peracetic acid, buffered to pH 7.2), and rapidly frozen. The third is rinsed in tap water, delaminated to the tela submucosa, rinsed in purified water, disinfected according to the methods of Example 2 in U.S. Pat. No. 5,460,962 (treatment in 0.1% by volume peracetic acid in high salt solution, buffered to pH 7.2), and rapidly frozen. All three samples were tested for endotoxins. The endotoxin levels were <0.14 EU/g for the first sample, >24 EU/g for the second sample, and >28 EU/g for the third sample.

EXAMPLE 6

Two sections of porcine small intestine were infected with $7 \times 10^6$ plaque forming units (PFU) of virus. Both were exposed to a 0.18% peracetic acid, 4.8% aqueous ethanol solution at a nine-to-one weight ratio of solution to material. A first sample was immersed in this solution for 5 minutes; the second was immersed for 2 hours. The material processed for 5 minutes exhibited 400 PFU per gram of material. The material processed for 2 hours exhibited zero PFU per gram of material.

EXAMPLE 7

Purified tela submucosa, prepared as described herein, was tested to determine its nucleic acid content. Four samples of material weighing 5 mg each were subjected to DNA/RNA extraction as detailed in the DNA/RNA Isolation Kit by Amersham Lifescience Inc., Arlington Heights, Ill. Nucleic acid quantitation was performed by spectrophotometric determination of solution optical densities at 260 nm and 280 nm. The average nucleic acid content was 1.9±0.2 mg per milligram of material.

Small intestinal submucosa, prepared as described by U.S. Pat. No. 4,902,508, was tested to determine its nucleic acid content. Four samples of material weighing 5 mg each were subjected to DNA/RNA extraction as detailed in the DNA/RNA Isolation Kit by Amersham. Nucleic acid quantitation was performed by spectrophotometric determination of solution optical densities at 260 nm and 280 nm. The average nucleic acid content was 2.4±0.2 mg per milligram of material.

EXAMPLE 8

Sections of tela submucosa prepared according to the methods described herein were sent to an independent testing laboratory (NAmSA, Inc., Northwood, Ohio) for biocompatibility testing as described in the standard ISO 10993. The samples were tested for USP Acute Systemic Toxicity, USP Intracutaneous Toxicity, Cytotoxicity, LAL Endotoxin, material-mediated Pyrogenicity, Direct Contact Hemolysis, and Primary Skin Irritation. The samples passed all tests, indicating that the material is biocompatible.

EXAMPLE 9

Using the procedure set forth in U.S. Pat. No. 5,460,962, two samples were analyzed. The first Kemp sample indicated an endotoxin level greater than 24 endotoxin units per gram and the second Kemp sample indicated an endotoxin level greater than 28 endotoxin units per gram. Thus, when using the procedure set forth in Kemp '962, the endotoxin levels fall outside the biocompatibility levels.

EXAMPLE 10

Using the procedures set forth in U.S. Pat. Nos. 4,902,508 and 5,372,821 issued to Badylak, the endotoxin level shown ranges as high as 23.9 endotoxin units per gram per sample. This falls outside the permissible range and thus does not the meet the criteria of biocompatibility. The invention, prepared in the above prescribed manner of disinfection first then delamination, was observed to have an endotoxin level of less than 12 endotoxin units per gram, and more particularly, reported an endotoxin level of less than 5 endotoxin units per gram. Thus, the material of the present invention is biocompatible as defined above.

EXAMPLE 11

Figures 2A, 2B:
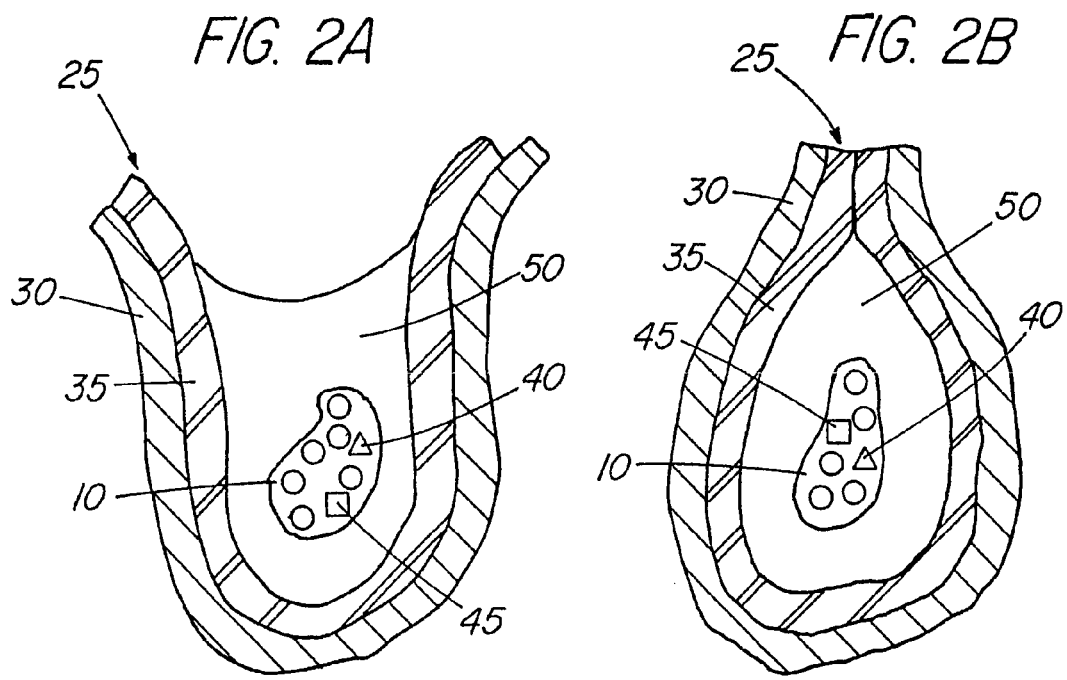
FIG. 2A shows one aspect of the invention as the biomaterial in a double pouched package, wherein the package is in an open configuration.
FIG. 2B shows one aspect of the invention as the biomaterial in a closed double pouched package.

With reference to FIGS. 2A and 2B, in preparing a lyophilized SIS sponge 10, comminuted SIS (with a mean particle size of approximately 150 μm) was centrifuged in a Beckman TJ-6 centrifuge with a speed of 1550×g for 15 minutes. The supernatant was poured off leaving a dough-like consistency of SIS remaining. The material was then poured into various polycarbonate molds and frozen at cold temperatures, preferably at −80° C. for at least 2 hours. The material was then vacuum-dried for 6 hours in a lyophilizing system with the condenser at −70° C. at a vacuum pressure of less than 100 millitorr, preferably 15 millitorr. Optionally, the sponge 10 can then be sterilized using ethylene oxide. The resulting structure was an SIS sponge 10, having a creamyish yellow-white color.

In varying the above procedures, the following attributes were noticed. Varying the "g" force from 0-15000×g, centrifugation at the higher "g" results in an increased sponge 10 density, a decreased sponge absorbency, and increased tensile strength. If the material were sterilized by radiation instead, for example using 10-25 kGy, noted was a decrease in tensile strength. Using comminuted hydrated SIS with a possible fragment size of 25 to 3000 μm produced a more condensed, higher density sponge, whereas larger fragments produced a less dense larger pore sized sponge. Adding sugar molecules to the comminuted hydrated SIS resulted in a increased pore size sponge. Furthermore, the addition of cross-linking agents, such as DANECOL, carbodiimide, or glutaraldehyde, caused an increased tensile strength that did not break down as easily upon the addition of water. In addition, moderating the pH of the suspension, from 2-10, preferably 3-5, demonstrated that a higher pH will reduce the tensile strength of the sponge. Since the resulting sponge can take the shape of the mold in which it is placed, modifying the mold shape will modify the sponge shape.

The resulting sponge finds applicability, inter alia, in providing hemostasis in a large wound; fills a large defect; provides a three dimensional structure for cell culture or in vivo growth; provides a plug to stop bleeding; can be an injectable form; can be used for vessel embolization.

EXAMPLE 12

In accordance with the present invention, the lyophilized SIS was compared to other forms of SIS to provide the following data:

| | Single layered Lyoph- ilized Sheet | Non- Dewatered SIS sponge | Dewatered SIS Sponge | 4-Layered Lyoph- ilized Sheet | 4-Layered Vacuum- Pressed Sheet** |
|---|---|---|---|---|---|
| Absorbency Level (g water per g of sample)*** | 5.3 | 5.6 | 4.2 | 3.1 | 1.0 |
| Density (g/cm$^3$) | .26 | .16 | .20 | .26 | .65 |
| Load at Failure of 1 cm wide strip (gf) | 882 | 161 | 587 | 4501 | 5931 |
| Stress at failure (gf/cm$^2$) | 7737 | 57 | 1792 | 11,169 | 237,240 |

**The 4-layered sheet was made in accordance with U.S. Pat. No. 5,711,969 issued to Patel, Hiles, Whitson, Cheng, Badylak, and Kokini; and assigned to Purdue Research Foundation and Methodist Hospital, all of Indiana, USA. The material used was made in accordance with U.S. Pat. No. 4,902,508, issued to Badylak et al.
***British Pharmacopoeia, 1988, vol. II, App. XX-L, pA226.

Notably, with reference to FIG. 1, the increasing number of lyophilized sheets 15 used indicated a decrease in the absorbency level to approximately 1.01 grams of water per gram of sample. Furthermore, by increasing the amount of water centrifuged out, the density increased.

EXAMPLE 13

With reference to FIG. 1, to prepare lyophilized multilaminate sheets 15, a sheet 20 of hydrated SIS was laid down on a non-stick surface, such as polytetrafluoroethylene (TEFLON®) and smoothed to remove any ripples or entrapments between the sheet 20 and the non-stick surface. A second sheet was placed over the first sheet and smoothed out in the same fashion. The process was repeated until the preselected number of sheets 20 were stacked forming the multilaminate sheet structure 15. A thin layer of high purity water was glazed over the top sheet of SIS and the material was frozen at −80° C. for at least 2 hours. The material was then vacuum dried at a vacuum pressure less than 100 millitorr (preferably less than 15 millitorr) in a condenser operating at −70° C. for six hours. The dried sheets were then cut into a preselected shape, sealed in packaging, and terminally sterilized using ethylene oxide.

By modifying the process in the manner described in Example 11, the sheet may have different attributes. For example, it was noted that adjusting the pH of the hydrated SIS to between 2-10, preferably 3-5, demonstrated an increased lamination strength. In addition, a tissue glue may be present between the sheets to increase lamination strength.

EXAMPLE 14

In making the SIS into various forms and lyophilizing the product, it was noted that the porosity index of the SIS changed. A sheet of hydrated SIS was attached to the bottom of a water column exerting a hydrostatic pressure of approximately 35 inches. The amount of water collected via pass through after 30 seconds was measured. The experiment was repeated using a single sheet of lyophilized SIS under the water column. In comparing the hydrated form of a single sheet of SIS with the lyophilized form, the hydrated form had a mean of 9.59 grams of water collected, with a standard deviation of 5.22. The lyophilized form had a mean of 0.2 grams of water with a standard deviation of 0.13.

With reference to FIGS. 2A and 2B, as with the lyophilized product, the product can be packaged in packages that are, inter alia, gas permeable, hermetically sealed, sterile, sealed, UV protected, double pouched, or some combination thereof. By UV barriered or UV protected, it is meant that the packages or pouches are made of a material that substantially blocks the contents from UV radiation. For example, the package can comprise the material disclosed in U.S. Pat. No. 5,489,022, which issued on 6 Feb. 1996 to Sabin Corp. (Bloomington, Ind.), the disclosure of which is entirely incorporated by reference herein. Preferably, the product is packaged in gas permeable double pouched packages that have a UV barrier to protect the internal product by placing the product in the package and sealing it. Gas permeable packages are desirable as it facilitates terminal sterilization with ethylene oxide. A double pouched package system 25 is desirable in that it permits the user to open the exterior pouch 30 and drop the inner pouch 35 on sterile surfaces. However, the packaging may include a plurality of pouches nested within each other, such that there is a pouch within a pouch within a pouch, etc. with the biomaterial being in the inner or innermost pouch. By sterile, it is meant that the package is sterilized and is of such construction and material as to keep the contents of the package and inner pouches sterile. The package can also contain a buffered solution 50 to keep the product wet. The solution can also contain the pharmocologic agents described above to permit long-term infiltration of the agent into the collagenous biomaterial product. The solution chosen can also include the characteristic that the final package can be terminally sterilized and thus sterilize the solution without deleteriously changing the solution characteristics.

In another embodiment of the invention, the medical device product comprises a submucosa of a warm blooded vertebrate made in the manner described above. The submucosa has an endotoxin level less than 12 endotoxin units per gram of submucosa and the submucosa further having an absorbency level of greater than 1.01 grams of water per gram of submucosa. The collagenous biomaterial further made by the process comprising the steps of sterilizing a source of submucosal tissue from the sources identified above; delaminating the source of submucosal tissue to expose the submucosa; freezing the submucosa in the manners described above; and drying the submucosa under vacuum pressure. Optionally, the collagenous biomaterial may be comminuted by grinding, shearing, or fragmenting the biomaterial in the manner described above. In addition, the collagenous biomaterial can further include packaging the biomaterial in at least one of a gas permeable, sealed, hermetically sealed, sterile, UV protected, and a plurality of pouches.

The collagen biomaterial can be made radiopaque by a variety of conventional procedures, none of which has yet been applied to tela submucosa. In one embodiment of the invention, the collagen material has a shape, namely made into sheets, either in lyophilized or non-lyophilized form. With reference to FIGS. 1, 2A, and 2B, any radiopaque substance 40, including but not limited to, tantalum such as tantalum powder, can be spread along the surface of the tela submucosa, such as on the serosal side. Other radiopaque materials 40 comprise bismuth and barium, including but not limited to, bismuth oxychloride and barium sulphate, as well as other conventional markers. As used herein, the term "disposed" on shall be construed to include disposed on, disposed throughout, disposed in, disposed with, disposed along with, applied on, applied with, applied through, applied in, applied in conjunction with, and the like. With particular reference to tela submucosa, the differential porosity of the material can enable more radiopaque material 40 to be disposed on the tela submucosa.

In one particular embodiment, radiopaque marker tantalum powder was disposed on a sheet of tela submucosa by rubbing it onto the serosal side of the tela submucosa. The tela submucosa was then made into various shapes, such as, but not limited to, having the shape of a brush-like, braided, branched, helical, spherical, cubic, cylindrical, tubular, injectable, randomized, layered, and sheet-like shapes. For example, an injectable shape of the invention can be readily made by comminuting the invention into small fibrils, fragments, or the like, then suspending them in solution, such as, but not limited to, a biocompatible gelatin suspension. Due to the viscosity of the gelatin suspension, the invention, when injected into the lumen of an aneurysm, will stay in the lumen and provide the therapeutic benefit to the aneurysm.

The invention and collagenous biomaterial can be made in layers. In this manner, the collagenous material can increase its structural integrity, strength, and applicability. In one embodiment of the invention, a dual layer of collagenous biomaterial can be used in sheets and either the radiomarker or pharmacologic agent, or both can be disposed in between the layers.

In similar fashion, the pharmacologic agent 45 can be disposed on the collagenous material. As used herein, the pharmacologic agent 45 includes, but is not limited to, growth factors, proteins, proteoglycans, glycosaminoglycans, physiological compatible minerals, antibiotics, chemotherapeutic agents, enzymes, drugs, and hormones. The agent can be disposed on the serosal or mucosal sides of the submucosa, or can be disposed on the same or opposite sides of the collagenous material. Consideration of placement can be important depending on the desired shape of the final device. For example, where the shape is tubular, it can be desirable to place the pharmacologic agent 45 on the abluminal surface since that surface will be in contact with the surrounding tissue. On the other hand, if systemic release of the agent 45 is contemplated, then the agent can be placed on the lumenal side to permit the blood to contact the agent and carry it away. Utilizing the braid shape, each individual strip can be treated with different agents.

It will be appreciated that variations of the above-described processing procedures are intended to be within the scope of this invention. For example, the source tissue for the collagenous biomaterial, e.g., stomach, whole intestine, cow uterus and the like, can be partially delaminated, treated with a disinfecting or sterilizing agent followed by complete delamination of the tela submucosa. Illustratively, attached mesentery layers, and/or serosa layers of whole intestine can be advantageously removed prior to treatment with the disinfecting agent, followed by delamination of remaining attached tissues from the tela submucosa These steps can or can not be followed by additional disinfection steps, e.g., enzymatic purification and/or nucleic acid removal. Alternatively, the tela submucosa source can be minimally treated with a disinfecting or other such agent, the tela submucosa delaminated from the tunica muscularis and tunica mucosa, followed by a complete disinfection treatment to attain the desired contaminant level(s). All such variations and modifications are contemplated to be a part of the process described herein and to be within the scope of the invention.

Many alterations and modifications can be made by those of ordinary skill in the art without departing from the spirit and scope of the invention. The illustrated embodiments have been shown only for purposes of clarity and examples, and should not be taken as limiting the invention as defined by the appended claims, which include all equivalents, whether now, or later devised.

What is claimed is:

1. A method for forming a collagenous biomaterial medical sponge device, comprising:
   providing a material including comminuted submucosa fragments and water, wherein said submucosa retains at least one biotropic agent, and wherein said biotropic agent includes a growth factor;
   placing said material in a mold;
   freezing said material in the mold; and
   drying said material in the mold to form a dried collagenous biomaterial medical sponge device, wherein said dried collagenous biomaterial medical sponge device retains at least one growth factor of the submucosa.

2. The method of claim 1, wherein said at least one biotropic agent also includes a proteoglycan.

3. The method of claim 2, wherein said at least one biotropic agent also includes a glycosaminoglycan.

4. The method of claim 1, wherein the submucosa is selected from intestinal submucosa, urinary bladder submucosa, and stomach submucosa.

5. The method of claim 4, wherein said submucosa is intestinal submucosa, and wherein the intestinal submucosa is small intestinal submucosa.

6. The method of claim 5, wherein the small intestinal submucosa is porcine.

7. The method of claim 1, also comprising crosslinking said material with a crosslinking agent after said freezing and drying.

8. The method of claim 7, wherein the crosslinking agent comprises a carbodiimide.

9. The method of claim 7, wherein the crosslinking agent comprises glutaraldehyde.

10. The method of claim 7, wherein the submucosa retains at least one biotropic agent selected from a proteoglycan, a glycosaminoglycan and a growth factor.

11. The method of claim 1, wherein the submucosa comprises attached lamina muscularis mucosa and stratum compactum.

12. A method for forming a collagenous biomaterial medical sponge device, comprising:
    providing a material including comminuted collagenous matrix fragments and water, said collagenous matrix obtained from a collagenous tissue source and retaining biotropic agents including a proteoglycan, a glycosaminoglycan and a growth factor from said tissue source;
    freezing said material; and
    drying said material to form a dried collagenous biomaterial medical sponge device, wherein said dried collagenous biomaterial medical sponge device retains at least one proteoglycan, glycosaminoglycan, and growth factor from said tissue source.

13. The method of claim 12, also comprising crosslinking said material with a crosslinking agent after said freezing and drying.

14. The method of claim 13, wherein the crosslinking agent comprises a carbodiimide.

15. The method of claim 13, wherein the crosslinking agent comprises glutaraldehyde.

16. A method for forming a collagenous biomaterial medical sponge device, comprising:
    providing a material including comminuted submucosa tissue fragments and water, wherein the submucosa tissue retains at least one biotropic agent, and wherein said biotropic agent includes a growth factor;

centrifuging said material to remove water;

after said centrifuging, positioning the comminuted submucosa tissue fragments in a mold;

freezing said comminuted submucosa tissue fragments in said mold; and drying said comminuted submucosa tissue fragments in said mold to form a dried collagenous biomaterial medical sponge device, wherein said dried collagenous biomaterial medical sponge device retains at least one growth factor of the submucosa.

17. The method of claim 16, also comprising crosslinking said material with a crosslinking agent after said drying.

18. The method of claim 17, wherein the crosslinking agent comprises a carbodiimide.

19. The method of claim 17, wherein the crosslinking agent comprises glutaraldehyde.

20. The method of claim 16, wherein the at least one biotropic agent also includes a glycosaminoglycan and a proteoglycan.

21. The method of claim 16, wherein the submucosa tissue comprises attached lamina muscularis mucosa and stratum compactum.

* * * * *